(12) United States Patent
Stalcup et al.

(10) Patent No.: US 11,918,478 B2
(45) Date of Patent: Mar. 5, 2024

(54) ADJUSTED STIFFNESS ORTHOPAEDIC IMPLANTS AND METHOD OF MANUFACTURE

(71) Applicant: SMed-TA/TD, LLC, Columbia City, IN (US)

(72) Inventors: Gregory C. Stalcup, Fort Wayne, IN (US); Paul S. Nebosky, Fort Wayne, IN (US); Kreigh R. Williams, Fort Wayne, IN (US)

(73) Assignee: SMed-TA/TD, LLC, Columbia City, IN (US)

( * ) Notice: Subject to any disclaimer, the term of this patent is extended or adjusted under 35 U.S.C. 154(b) by 270 days.

(21) Appl. No.: 17/391,243

(22) Filed: Aug. 2, 2021

(65) Prior Publication Data

US 2021/0353425 A1 Nov. 18, 2021

Related U.S. Application Data

(62) Division of application No. 16/704,698, filed on Dec. 5, 2019.

(60) Provisional application No. 62/775,498, filed on Dec. 5, 2018.

(51) Int. Cl.
*A61F 2/44* (2006.01)
*A61F 2/30* (2006.01)

(52) U.S. Cl.
CPC ....... *A61F 2/44* (2013.01); *A61F 2002/30011* (2013.01); *A61F 2002/30014* (2013.01); *A61F 2002/3093* (2013.01)

(58) Field of Classification Search
CPC .. A61F 2/44; A61F 2/442; A61F 2/444; A61F 2/4455; A61F 2/3094; A61F 2/30965; A61F 2002/30942; A61F 2002/3096; A61F 2002/30965; A61F 2002/30971; A61F 2002/30973; A61F 2002/3097; A61F 2002/30963

See application file for complete search history.

(56) References Cited

U.S. PATENT DOCUMENTS

| | | | |
|---|---|---|---|
| 5,064,439 A * | 11/1991 | Chang | B29C 70/222 623/23.51 |
| 2001/0039455 A1 * | 11/2001 | Simon | A61F 2/30767 623/18.11 |
| 2003/0139815 A1 * | 7/2003 | Grooms | A61F 2/4644 623/17.11 |
| 2003/0187506 A1 | 10/2003 | Ross et al. | |
| 2004/0068320 A1 | 4/2004 | Robie et al. | |
| 2005/0112397 A1 * | 5/2005 | Rolfe | A61F 2/4455 606/76 |
| 2005/0221258 A1 * | 10/2005 | Hall | A61C 8/0012 433/173 |

(Continued)

OTHER PUBLICATIONS

Extended European Search Report dated Apr. 7, 2020 for European Patent Application No. 19 21 3660 (9 pages).

*Primary Examiner* — Matthew J Lawson
(74) *Attorney, Agent, or Firm* — Taylor IP, P.C.

(57) ABSTRACT

A method of manufacturing multiple orthopaedic implants includes: producing a strip of material including a composite of a first porous ingrowth material and a second porous ingrowth material; forming a plurality of through-openings in the strip; and cutting a plurality of implant blanks from the strip, each of the implant blanks including at least one of the formed through-openings.

16 Claims, 8 Drawing Sheets

(56) References Cited

U.S. PATENT DOCUMENTS

| | | |
|---|---|---|
| 2006/0235542 A1 | 10/2006 | Hodorek et al. |
| 2008/0188945 A1* | 8/2008 | Boyce ................ A61B 17/0401 |
| | | 623/23.61 |
| 2011/0022180 A1* | 1/2011 | Melkent ................ A61L 31/121 |
| | | 427/2.27 |
| 2011/0045087 A1* | 2/2011 | Kerr ........................ A61L 27/56 |
| | | 424/490 |
| 2011/0071635 A1* | 3/2011 | Zhang ..................... B32B 15/08 |
| | | 606/279 |
| 2011/0190888 A1* | 8/2011 | Bertele ................... A61F 2/447 |
| | | 623/17.11 |
| 2012/0191190 A1 | 7/2012 | Trieu |
| 2012/0312779 A1* | 12/2012 | Patterson ................ B29C 59/16 |
| | | 451/28 |
| 2013/0166028 A1 | 6/2013 | Shieh et al. |
| 2014/0094919 A1 | 4/2014 | Mantri |
| 2014/0277461 A1 | 9/2014 | Nebosky et al. |
| 2016/0199193 A1 | 7/2016 | Willis et al. |
| 2018/0049886 A1* | 2/2018 | Black ...................... A61F 2/447 |
| 2019/0133783 A1 | 5/2019 | Unger et al. |
| 2019/0142600 A1 | 5/2019 | Tipping |
| 2019/0231537 A1* | 8/2019 | Umstadt ................... A61F 2/28 |
| 2019/0314169 A1* | 10/2019 | Patel ..................... A61F 2/4455 |
| 2019/0328539 A1 | 10/2019 | Suh et al. |
| 2020/0197565 A1 | 6/2020 | Suh et al. |
| 2020/0289714 A1* | 9/2020 | Snell ...................... B29C 43/02 |

* cited by examiner

ADJUSTED STIFFNESS ORTHOPAEDIC IMPLANTS AND METHOD OF MANUFACTURE

CROSS REFERENCE TO RELATED APPLICATIONS

This is a division of U.S. patent application Ser. No. 16/704,698, entitled "ADJUSTED STIFFNESS ORTHOPAEDIC IMPLANTS AND METHOD OF MANUFACTURE," filed Dec. 5, 2019, which is incorporated herein by reference. U.S. patent application Ser. No. 16/704,698 is a non-provisional application based upon U.S. Provisional Patent Application Ser. No. 62/775,498, entitled "ADJUSTED STIFFNESS ORTHOPAEDIC IMPLANTS AND METHOD OF MANUFACTURE", filed Dec. 5, 2018, which is incorporated herein by reference.

BACKGROUND OF THE INVENTION

1. Field of the Invention

The present disclosure relates to medical implants and, more particularly, to orthopaedic implants.

2. Description of the Related Art

Orthopaedic implants are commonly used to replace and/or repair anatomical structures of a patient that have been damaged due to disease and/or injury. To be successful, the implant needs to have sufficient strength. If the strength of the implant is not sufficient, the implant can fail and require a revision. While known implants can be successful, implant failure rates and the rate of adverse patient events remain higher than desired.

What is needed in the art is an implant that can address some of the previously described issues of known implants.

SUMMARY OF THE INVENTION

Exemplary embodiments disclosed herein provide orthopaedic implants with an implant stiffness that can be adjusted based on patient requirements.

In some exemplary embodiments disclosed herein, a method of manufacturing multiple orthopaedic implants is provided. The method includes: producing a strip of material comprising a composite of a first porous ingrowth material and a second porous ingrowth material; forming a plurality of through-openings in the strip; and cutting a plurality of implant blanks from the strip, each of the implant blanks comprising at least one of the formed through-openings.

One possible advantage that may be realized by exemplary embodiments disclosed herein is that the stiffness of the orthopaedic implant may be adjusted to match the specific requirements of a patient to reduce the risk of providing an overly stiff implant.

Another possible advantage that may be realized by exemplary embodiments disclosed herein is that the orthopaedic implants may be produced in an economical manner.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
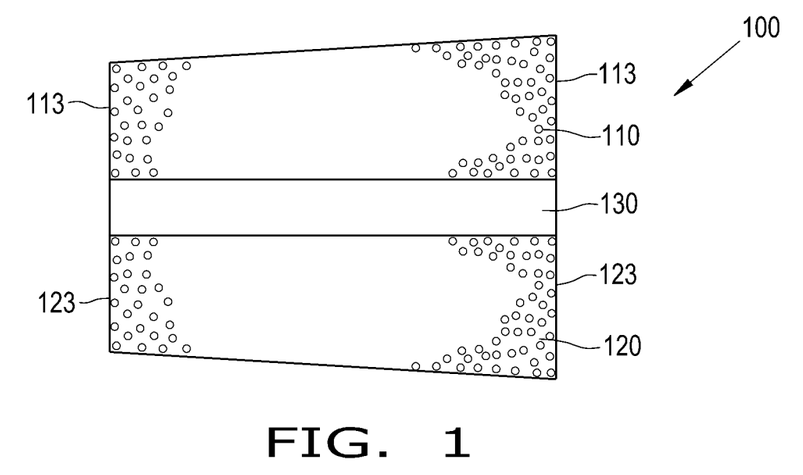
FIG. 1 is a side view of an exemplary embodiment of an orthopaedic implant including an intermediate region, provided according to the present disclosure.
Figure 2:
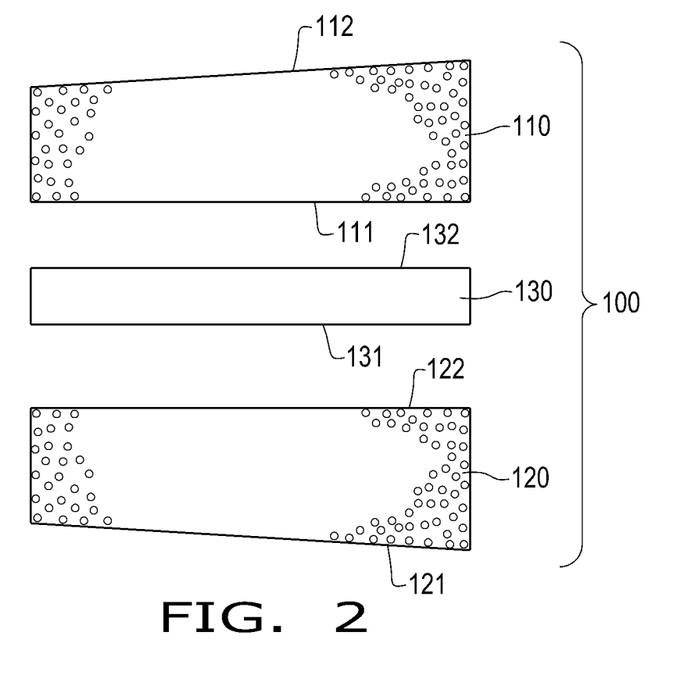
FIG. 2 is an exploded view of the orthopaedic implant of FIG. 1.

Referring now to the drawings, and more particularly to FIGS. 1-2, an exemplary embodiment of an orthopaedic implant 100 is illustrated. The orthopaedic implant 100 has the general shape of a spinal implant, such as a vertebral implant, for implantation within the spine of a human or a non-human animal. As illustrated, the implant 100 includes a first porous ingrowth material region 110, a second porous ingrowth material region 120, and a separate porous or nonporous intermediate region 130 disposed between the ingrowth material regions 110, 120. As used herein, an "intermediate region" may also be referred to as a "stiffness modulating region" and/or a "stiffness adjusting region." The intermediate region 130 has a top surface 132 connected to a bottom surface 111 of the material region 110 and a bottom surface 131 connected to a top surface 122 of the material region 120. As illustrated, the top surface 132 and the bottom surface 131 of the intermediate region 130 are both substantially flat, i.e., planar, so the orthopaedic implant 100 is a "flat" spinal implant. The bottom surface 111 of the material region 110 and the top surface 122 of the material region 120 are similarly flat. A top surface 112 of the material region 110 and a bottom surface 121 of the material region 120, on the other hand, may be angled to conform to the natural anatomical shape of vertebrae that will bear on the respective surfaces 112, 121. The material regions 110 and 120 may also have respective peripheral surfaces, such as surfaces 113 and 123, that are substantially planar with one another and a peripheral surface 133 of the intermediate region 130. In some embodiments, a through-hole (not seen) may be formed through the implant 100 that extends from the top surface 112 of the material region 110 through the intermediate region 130 and to the bottom surface 121 of the material region 120. It should be appreciated that while the implant 100 is illustrated and described as having three distinct regions 110, 120, 130, in some embodiments the implant 100 has fewer than three regions, i.e., one or two regions, or more than three regions, e.g., four, five, or more than five regions. Further, while the implant 100 is illustrated and described as a spinal implant, the implant may be formed as a different type of orthopaedic implant, such as a knee implant, in accordance with the present disclosure.

The material regions 110 and 120 may comprise a similar, or the same, biocompatible material that is porous to encourage tissue ingrowth and fixation of the implant 100. Exemplary materials that may be used to form the material regions 110 and 120 include, but are not limited to: metals such as titanium, stainless steel, cobalt chrome, and/or tantalum; polymers such as ultra-high molecular weight polyethylene (UHMWPE), other forms of polyethylene, polyaryl ether ketone (PAEK) such as polyether ether ketone (PEEK), polycarbonate urethane (PCU), polylactic acid (PLA), and/or polyglycolic acid (PGA); and/or ceramics such as hydroxyapatite (HA), high-density alumina, so-called "Bioglass," and graphite. The porosity of the material regions 110, 120 may be varied to alter tissue ingrowth characteristics into the material regions 110, 120. The porosity of the material regions 110, 120 may be, for example, between 30% and 70% to encourage tissue ingrowth into the material regions 110, 120. An exemplary material that may be used to form the material regions 110, 120 is commercially available under the tradename OSTEOSYNC® from SITES MEDICAL® of Columbia City, Indiana.

The intermediate region 130 may also comprise a porous biocompatible material, similar to the material regions 110, 120, that has a different stiffness, which may be either higher or lower, than the material regions 110, 120. In this sense, the intermediate region 130 may act as a stiffness modulating core to provide the implant 100 with the desired stiffness, which will typically be different than the stiffness in material regions 110, 120. As used herein, the "stiffness" of the material corresponds to the Young's modulus (E) of the material(s) of the regions 110, 120, 130. In some embodiments, the intermediate region 130 comprises a relatively high stiffness material, compared to the material regions 110, 120, such as titanium, cobalt chrome, PEEK, or polycarbonate urethane. The stiffness of the intermediate region 130 may be higher than the material regions 110, 120 due to, for example, the intermediate region 130 having a different material composition with a generally stiffer material than the material regions 110, 120, changing the shape of the intermediate region 130 compared to the material regions 110, 120, and/or by forming the material regions 110, 120 and/or the intermediate region 130 with stiffness adjusting features, as will be described further herein. In some embodiments, the intermediate region 130 comprises the same material composition as the material regions 110, 120 but is formed with a lower porosity so the intermediate region 130 has a greater stiffness than the material regions 110, 120. In some embodiments, the intermediate region 130 comprises a relatively low stiffness material, compared to the material regions 110, 120, to lower the overall stiffness of the implant 100. It should be appreciated that the intermediate region 130 may also comprise one or more regions of a relatively high stiffness material as well as one or more regions of a relatively low stiffness material to provide the desired stiffness characteristics.

Figure 3:
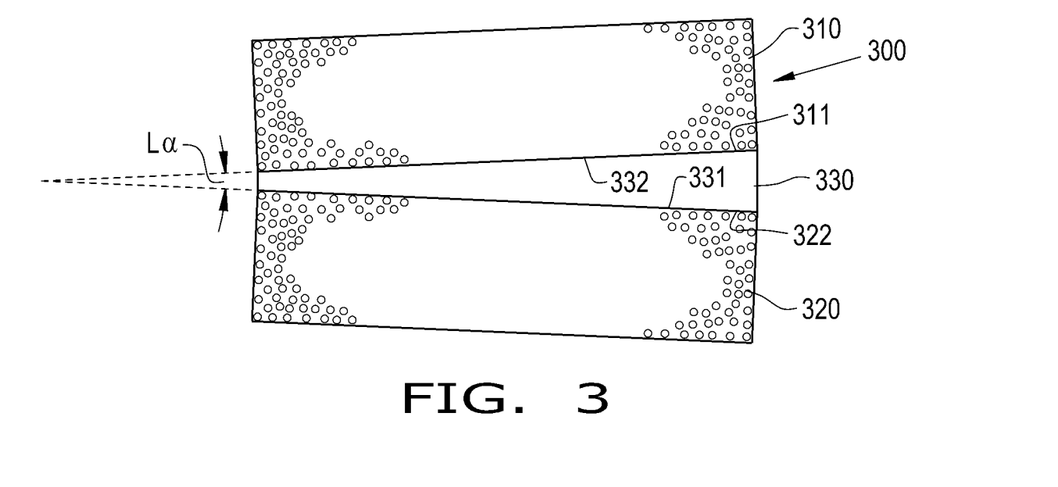
FIG. 3 is a side view of an exemplary embodiment of an orthopaedic implant including a tapered intermediate region, provided according to the present disclosure.

Referring now to FIG. 3, another exemplary embodiment of an orthopaedic implant 300 is illustrated that is similar to the orthopaedic implant 100 but is formed with a porous intermediate region 330 with a tapered bottom surface 331 and a tapered top surface 332 to define a lordotic angle La. The intermediate region 330 is disposed between a first porous ingrowth material region 310 and a second porous ingrowth material region 320. The material region 310 may have a flat bottom surface 311 connected to the tapered top surface 332 of the intermediate region 330 and the material region 320 may have a flat top surface 322 connected to the tapered bottom surface 331 of the intermediate region 330. In this sense, the lordotic angle La defined by the tapered surfaces 331, 332 of the intermediate region 330 defines the lordotic angle of the implant 300. The intermediate region 330 may be formed to define a lordotic angle La ranging between, for example, 3° and 15°, depending on the patient anatomy at the implantation site. Other than the implant 300 being provided with the lordotic angle La, the implant 300 may be formed similarly to the implant 100 illustrated in FIGS. 1-2 and include the intermediate region 330 to modulate the implant stiffness, so further description is omitted for the sake of brevity.

Figure 4:
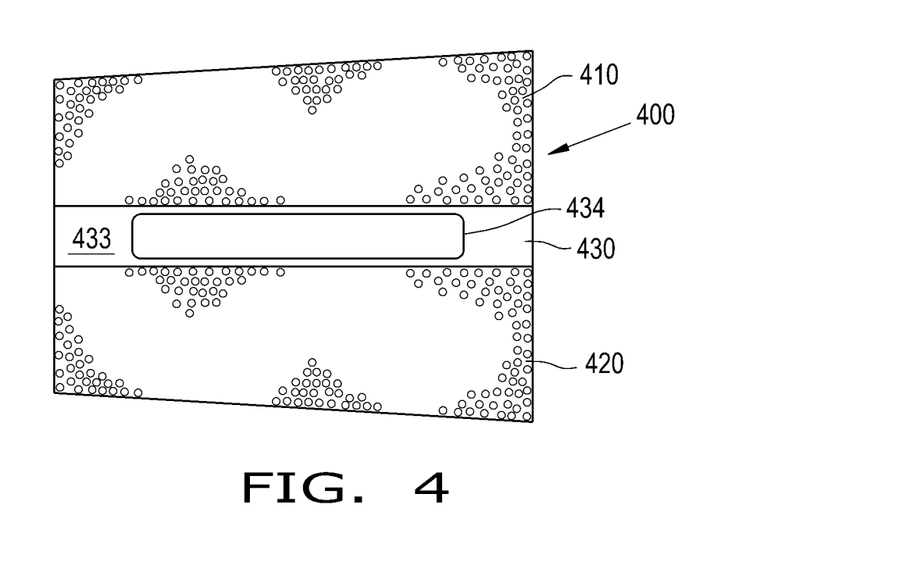
FIG. 4 is a side view of an exemplary embodiment of an orthopaedic implant including an intermediate region with a stiffness adjusting feature, provided according to the present disclosure.
Figure 5:
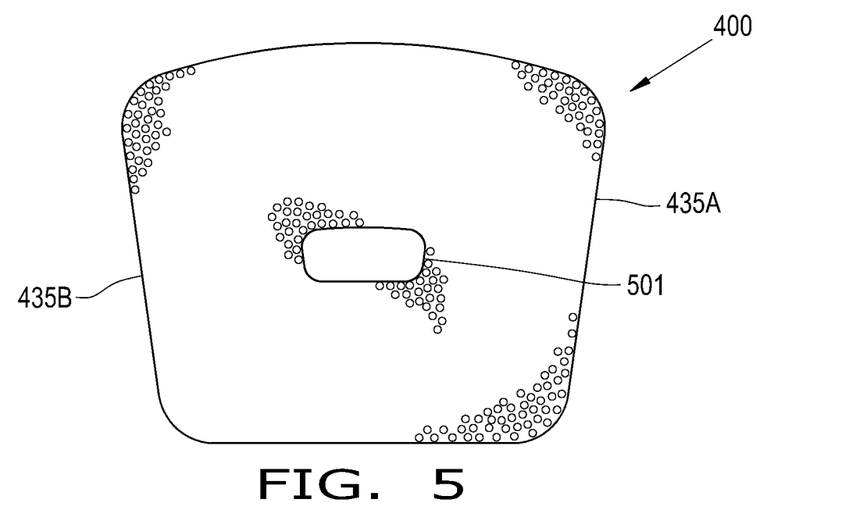
FIG. 5 is a top view of the orthopaedic implant of FIG. 4.

Referring now to FIGS. 4-5, another exemplary embodiment of an implant 400 formed according to the present disclosure is illustrated. The implant 400 may be formed as a flat spinal implant, similarly to the previously described implant, with a first porous ingrowth material region 410, a second porous ingrowth material region 420, and a porous intermediate region 430 disposed between the material regions 410 and 420. While illustrated as being formed as a flat implant, in some embodiments the implant 400 is provided with a lordotic angle.

The implant 400 may have a through-hole 501 (illustrated in FIG. 5) that extends from top to bottom through the ingrowth material regions 410, 420 and the intermediate region 430 as well as one or more additional openings 434 formed through a peripheral surface 433 of the intermediate region 430 to adjust the stiffness of the intermediate region 430, and thus the overall stiffness of the implant 400. In some embodiments, the additional opening 434, which may also be referred to as a "stiffness adjusting feature," extends through the intermediate region 430 from one side, such as side 435A, to an opposite side 435B of the intermediate region 430. In this respect, the stiffness adjusting feature 434 is a void formed in the intermediate region 430 that reduces the overall stiffness of the implant 400, the significance of which will be described further herein. The stiffness adjusting feature 434 defines a volume of material removed from the intermediate region 430 that may be adjusted to provide the implant 400 with a desired stiffness. The volume of material removed from the intermediate region 430 to obtain the desired stiffness may depend, for example, on the material composition of the intermediate region 430 as well as desired stiffness characteristics. It should thus be appreciated that while the stiffness adjusting feature 434 is illustrated as an opening of constant rectangular cross-section formed through the intermediate region 430, the stiffness adjusting feature 434 may have other cross-sectional shapes, which may vary through the intermediate region 430. Further, it should be appreciated that while the stiffness adjusting feature 434 is illustrated as being formed in the intermediate region 430, one or more stiffness adjusting features may also be formed in the material regions 410, 420. In other respects, the implant 400 may be similar to the previously described implants 100 and 300.

Figure 6A:
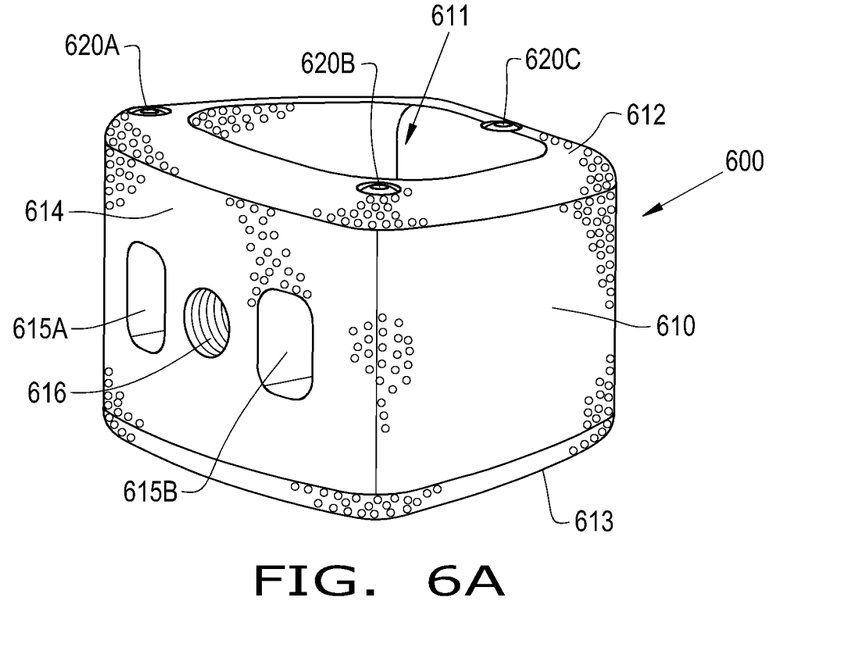
FIG. 6A is a perspective view of an exemplary embodiment of an orthopaedic implant including a plurality of reinforcement elements, provided according to the present disclosure.
Figure 6B:
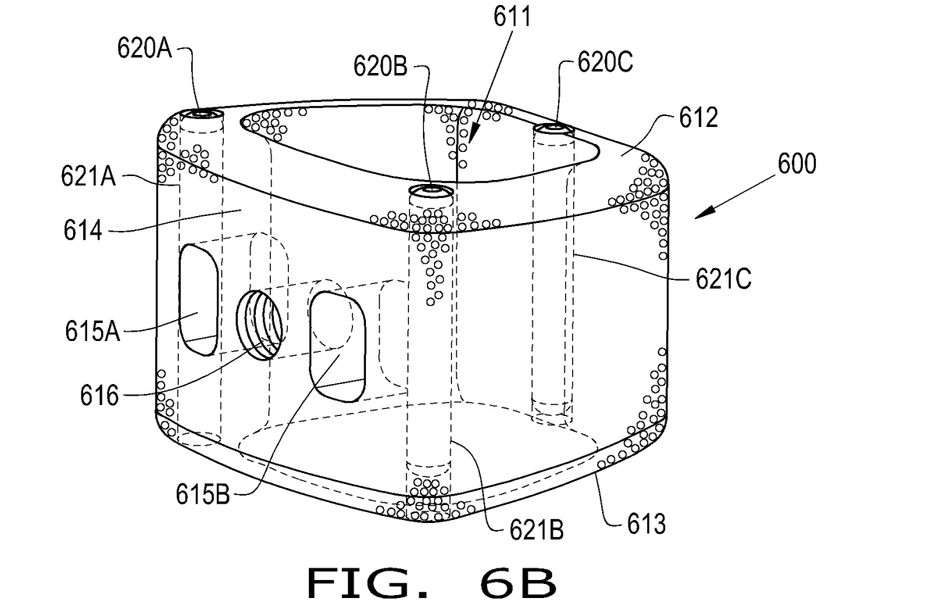
FIG. 6B is a partial cut-away view of the orthopaedic implant of FIG. 6A.

Referring now to FIGS. 6A and 6B, another exemplary embodiment of an orthopaedic implant 600 formed according to the present disclosure is illustrated. Unlike the previously described implants 100, 300, 400, the orthopaedic implant 600 may have a shape that is substantially formed with a single porous ingrowth material body 610, i.e., the implant 600 does not have a distinct porous intermediate region between two porous ingrowth material regions. The material body 610 may comprise similar materials to the previously described ingrowth material regions, such as ingrowth material region 110. As illustrated, the material body 610 may have a through-hole 611 extending through the material body 610 from a top surface 612 to a bottom surface 613, which may be a feature for bone graft placement and/or a stiffness adjusting feature that can change the overall stiffness of the material body 610. The material body 610 may also have one or more peripheral surfaces, such as peripheral surface 614, that is formed with one or more additional stiffness adjusting features, such as openings 615A, 615B, that extend through the peripheral surface 614. In some embodiments, the openings 615A, 615B are of similar size and shape and both extend to the through-hole 611. The peripheral surface 614 may also have a threaded opening 616 formed therein to, for example, couple with an instrument for placement of the implant 600 at an implantation site.

In some embodiments, the implant 600 further includes one or more reinforcing elements, shown as pins 620A, 620B, 620C, to increase the strength of the implant 600 in certain directions. As illustrated in FIG. 6B, for example, the pins 620A, 620B, 620C may be placed in corresponding pin openings 621A, 621B, 621C that extend from the top surface 612 toward the bottom surface 613 of the material body 610. The pins 620A, 620B, 620C may comprise, for example, titanium, PEEK, or another type of relatively high strength material. As can be appreciated, the material body 610 has a void (through-hole 611) formed therein with a significant volume. While the void 611 provides the material body 610 with desired bone graft placement and stiffness characteristics in, for example, medial-lateral and anterior-posterior directions, the torsional, shear, or compressive strength of the material body 610 may be insufficient without reinforcement. Thus, the pins 620A, 620B, 620C may be provided to reinforce the material body 610 in a direction of compression so the implant 600 has sufficient compressive strength to withstand normal loading without a significant risk of failure.

Figure 7:
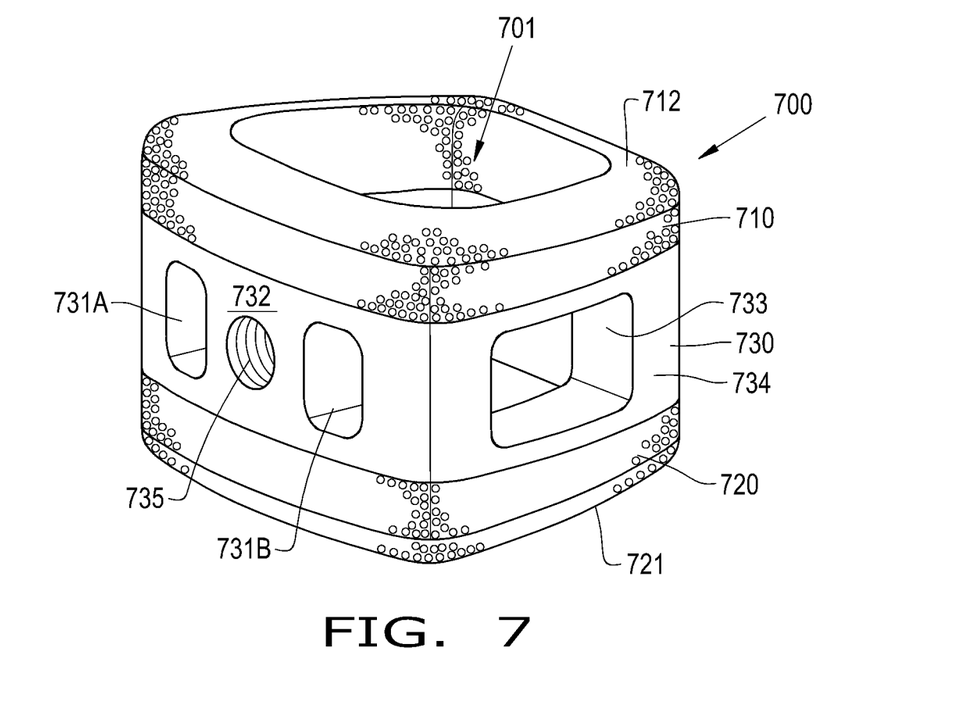
FIG. 7 is a perspective view of an exemplary embodiment of an orthopaedic implant including an intermediate region with a pair of stiffness adjusting features, provided according to the present disclosure.

Referring now to FIG. 7, another exemplary embodiment of an orthopaedic implant 700 formed according to the present disclosure is illustrated. The orthopaedic implant 700 has a similar shape to the implant 600 illustrated in FIGS. 6A-6B, but has a pair of porous ingrowth material regions 710, 720 with a porous or nonporous intermediate region 730 disposed between the material regions 710, 720, similarly to the previously described implants 100, 300, and 400. The material regions 710, 720 may comprise materials similar to, for example, previously described material regions 110, 120 and the intermediate region 730 may comprise materials similar to, for example, previously described intermediate region 130. In some embodiments, the material of the intermediate region 730 has a different stiffness than the material of the material regions 710 and 720.

The implant 700 may have a through-hole 701 extending from a top surface 712 of the material region 710 to a bottom surface 721 of the material region 720 through the intermediate region 730. The intermediate region 730 may also have a pair of stiffness adjusting features, illustrated as openings 731A, 731B, formed in a peripheral surface 732 and an additional stiffness adjusting feature, illustrated as another opening 733, formed in another peripheral surface 734. The openings 731A, 731B may have a same or similar size and shape relative to one another, but differ in size and shape from the opening 733. In this respect, the openings 731A, 731B, 733 formed in the intermediate region 730 can have different effects on the stiffness of the intermediate region 730, and thus the stiffness of the implant 700. In some embodiments, the peripheral surface 732 also has a threaded opening 735 formed therein to, for example, couple with an insertion tool for inserting the implant 700.

Figure 8:
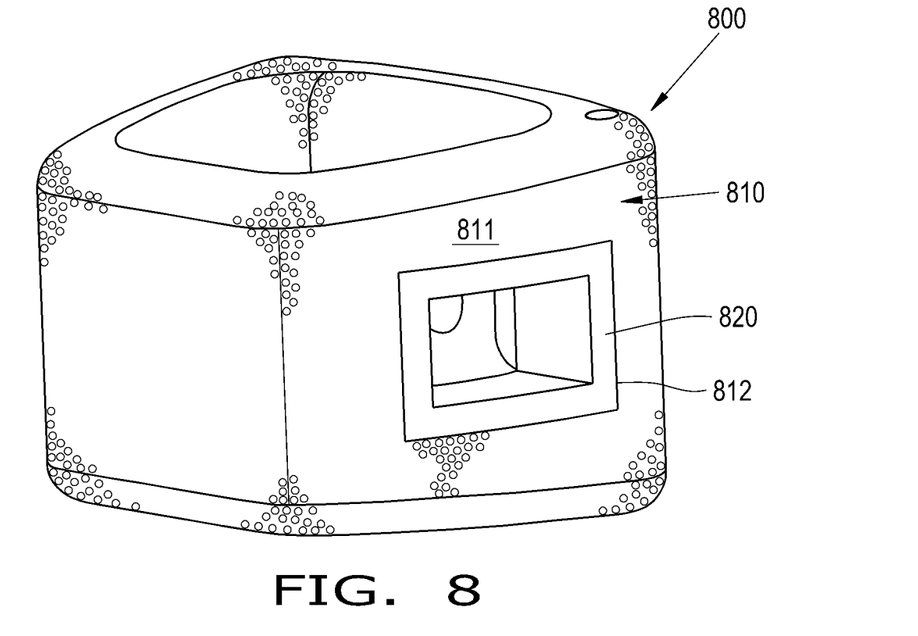
FIG. 8 is a perspective view of an exemplary embodiment of an orthopaedic implant including a cutout that has a reinforcing material disposed therein, provided according to the present disclosure.

Referring now to FIG. 8, another exemplary embodiment of an orthopaedic implant 800 formed according to the present disclosure is illustrated. The orthopaedic implant 800 may be formed with a single porous ingrowth material body 810, similarly to the previously described implant 600. The material body 810 may be formed with one or more peripheral surfaces 811 having a cutout 812 formed therein. A reinforcing material 820, which comprises a material with a higher strength than the material of the material body 810, may be placed in the cutout 812 to reinforce the implant 800 and increase the strength of the implant 800. In this respect, the reinforcing material 820 contacts boundary surfaces of the cutout 812 and acts similarly to a window frame to increase the strength of the material surrounding the cutout 812 rather than including, for example, reinforcing pins. In other respects, the implant 800 can be similar to the implant 600, so further description is omitted for brevity.

Referring now to FIGS. 9-12, additional exemplary embodiments of orthopaedic implants 900, 1000, 1100, 1200 formed according to the present disclosure are illustrated. As can be seen, each of the implants 900, 1000, 1100, 1200 includes a respective first porous ingrowth material region 910, 1010, 1110, 1210, a respective second porous ingrowth material region 920, 1020, 1120, 1220, and a respective porous or nonporous intermediate region 930, 1030, 1130, 1230 disposed between the material regions 910, 920, 1010, 1020, 1110, 1120, 1210, 1220. The material regions 910, 920, 1010, 1020, 1110, 1120, 1210, 1220 may comprise the same materials as, for example, the previously described material regions 110 and 120 and the intermediate regions 930, 1030, 1130, 1230 may comprise the same materials as, for example, the previously described intermediate region 130. As illustrated, the implants 900, 1000, 1100, 1200 can be formed to have a substantially domed shape. Each of the implants 900, 1000, 1100, 1200 can be formed with a through-opening 901, 1001, 1101, 1201 that extends from a top surface 902, 1002, 1102, 1202 to a bottom surface 903, 1003, 1103, 1203 of the implant 900, 1000, 1100, 1200. One or more reinforcing ribs 904A, 904B, 1004A, 1004B, 1104A, 1104B, 1204A, 1204B may be disposed in the void formed by the through-opening 901, 1001, 1101, 1201, rather than leaving the void empty. In some embodiments, the ribs 904A, 904B, 1004A, 1004B, 1104A, 1104B, 1204A, 1204B are formed as a result of forming the through-opening 901, 1001, 1101, 1201. Additionally, one or more stiffness adjusting features, such as openings 931A, 931B, 931C, 931D, 1031A, 1031B, 1031C, 1031D, 1131A, 1131B, 1231A, 1231B, 1231C, 1231D, may be formed in the intermediate region 930, 1030, 1130, 1230 and extend to the through-opening 901, 1001, 1101, 1201. Threaded openings 932A, 932B, 1032A, 1032B, 1132, 1232A, 1232B may also be formed in the intermediate region 930, 1030, 1130, 1230 to interact with an insertion tool for inserting the implant 900, 1000, 1100, 1200 at an implant site.

Figure 9:
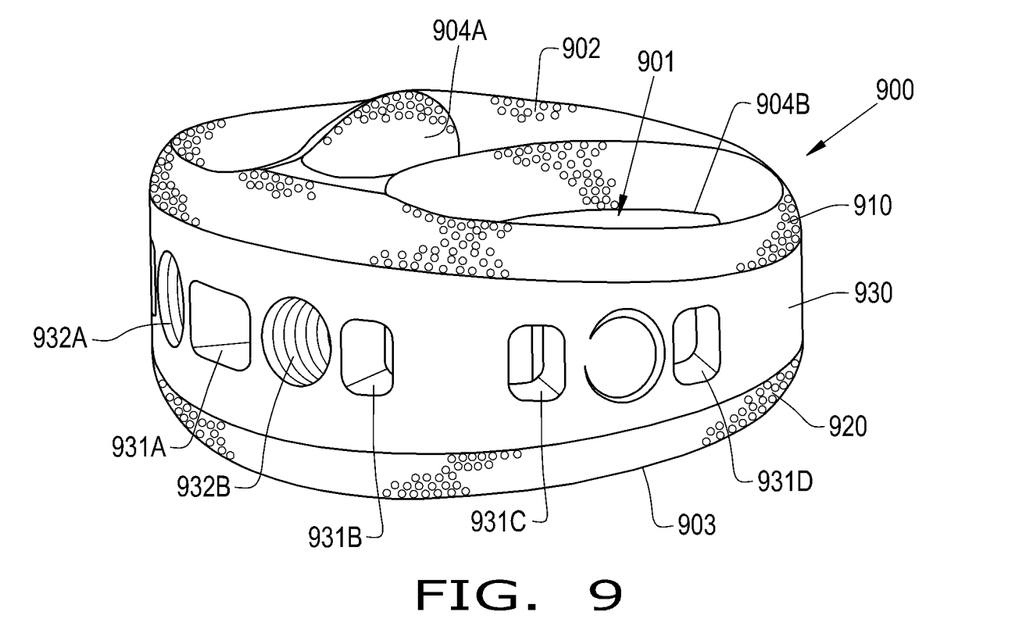
FIG. 9 is a perspective view of an exemplary embodiment of an orthopaedic implant including an intermediate region and a plurality of reinforcing ribs, provided according to the present disclosure.

Referring specifically now to FIG. 9, it may be seen that the implant 900 has reinforcing ribs 904A, 904B that may be formed of the same material as the intermediate region 930 to modify the stiffness of the implant 900 compared to, for example, if the void formed by the through-opening 901 was left empty. The ribs 904A, 904B may be partially covered by the material region 910 on top and the material region 920 on bottom. As illustrated, the ribs 904A, 904B may be solid, i.e., formed without voids therein.

Figure 10:
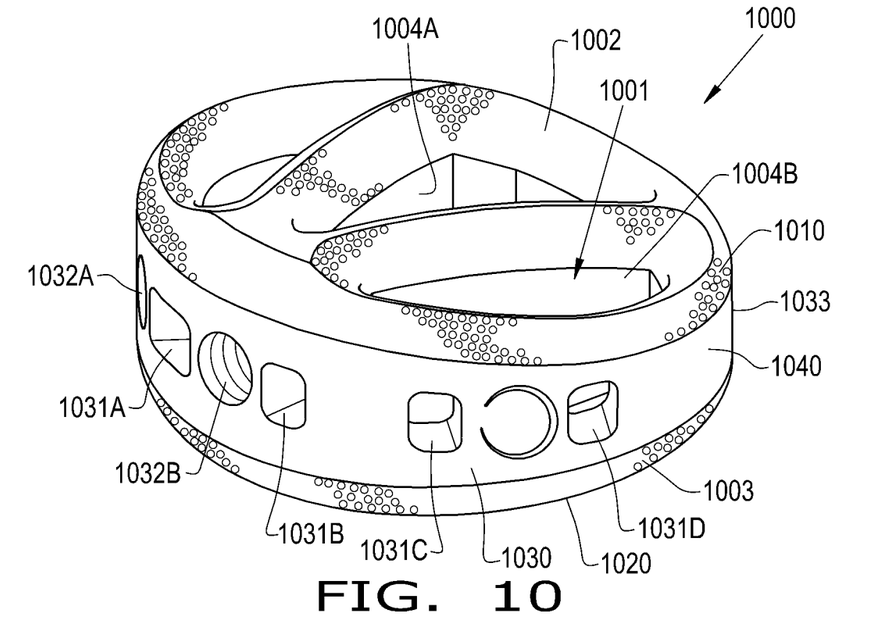
FIG. 10 is a perspective view of an exemplary embodiment of an orthopaedic implant including an intermediate region that is partially wrapped with a wrapping porous ingrowth material and a plurality of reinforcing ribs, provided according to the present disclosure.

Referring specifically now to FIG. 10, it may be seen that the intermediate region 1030 is "wrapped" with a porous ingrowth material region 1040 that may comprise a material similar to the material(s) of the material regions 1010, 1020. As illustrated, the wrapping material region 1040 may wrap around some or all of an outer diameter 1033 of the intermediate region 1030 to provide a more porous material on the intermediate region 1030 for tissue ingrowth. In other respects, the implant 1000 may be similar to the implant 900.

Figure 11:
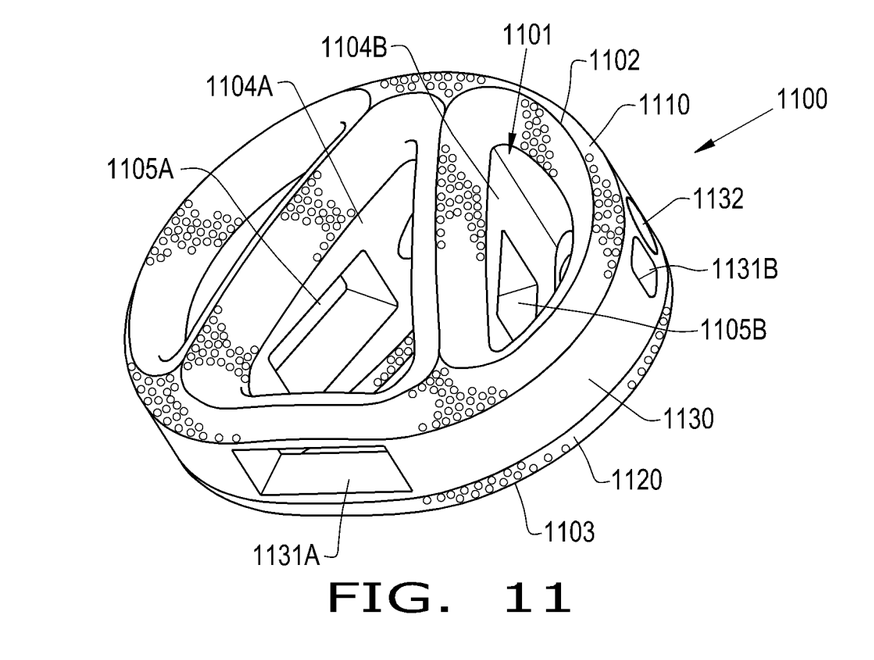
FIG. 11 is a perspective view of an exemplary embodiment of an orthopaedic implant including an intermediate region and a plurality of reinforcing ribs having rib cutouts, provided according to the present disclosure.

Referring specifically now to FIG. 11, it may be seen that the implant 1100 has reinforcing ribs 1104A, 1104B that are formed with rib cutouts 1105A, 1105B to decrease the stiffness of the respective ribs 1104A, 1104B. In all other respects, the implant 1100 may be similar to the implant 900.

Figure 12:
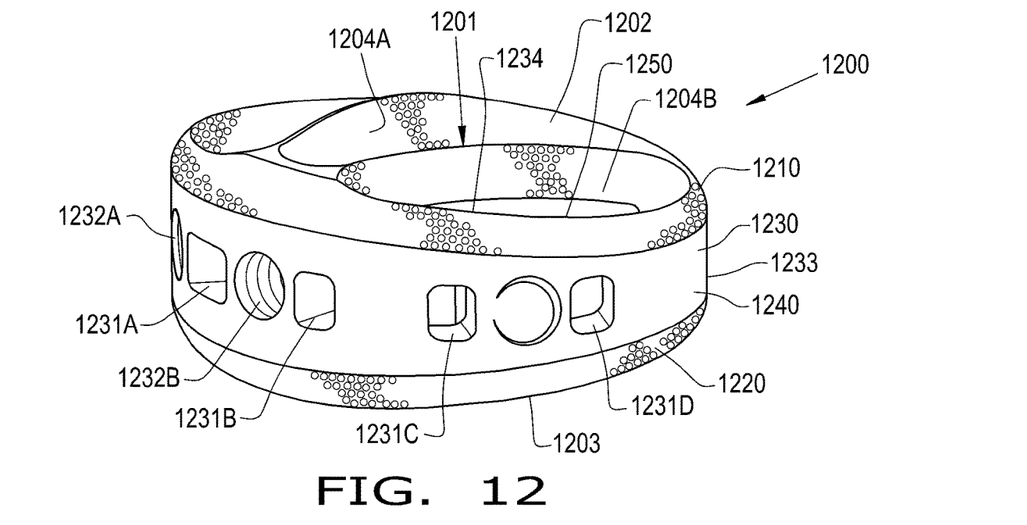
FIG. 12 is a perspective view of an exemplary embodiment of an orthopaedic implant including an intermediate region that is wrapped with a wrapping porous ingrowth material and a plurality of reinforcing ribs, provided according to the present disclosure.

Referring specifically now to FIG. 12, it may be seen that the intermediate region 1230 is "wrapped" with a porous ingrowth material region 1240 on some or all of an outer diameter 1233 of the intermediate region 1230, similarly to the intermediate region 1030 of the implant 1000. The implant 1200 further includes another porous ingrowth material region 1250 that is "wrapped" around some or all of an inner diameter 1234 of the intermediate region 1230, so both the outer diameter 1233 and the inner diameter 1234 of the intermediate region 1230 are at least partially wrapped in porous ingrowth material. In other respects, the implant 1200 may be similar to the implant 1000.

It has been found that, in many instances, the stiffness of an orthopaedic implant does not need to be as high as possible to promote healing of the patient. Rather, in certain instances the implant may be formed with too high of a stiffness to the detriment of the patient. For example, in spinal implants, the implant having an overly high stiffness can lead to vertebral endplates of the spine fracturing following implantation, even under loads that would not normally fracture the endplates. This type of fracturing is due to the overly high stiffness of the implant transmitting excessive loads to surrounding anatomical structures, rather than deforming to absorb some of the load. The excessive transmitted loads lead to instances where the surrounding bone is subjected to higher-than-normal stress, causing fracturing, when subjected to loads that normally would not cause fracturing.

On the other hand, the stiffness of the implant must be sufficiently high to support the surrounding anatomical structures. If the stiffness of the implant is too low, the implant does not provide the proper support for the spinal column, which can lead to abnormal curvature of the spine and significantly increase the risk of spinal injuries. Thus, the stiffness of the implant is of particular concern when designing the implant because too high or too low of a stiffness tends to increase the risk of adverse effects following implantation.

In the context of this finding, the implants 100, 300, 400, 600, 700, 800, 900, 1000, 1100, and 1200 formed according to the present disclosure may have a stiffness that falls within a range that is not too high, which could lead to abnormal bone fracturing, but also not so low that the surrounding anatomical structures are not adequately supported. The stiffness of the implants 100, 300, 400, 600, 700, 800, 900, 1000, 1100, and 1200 may be adjusted as previously described to provide the desired stiffness. Thus, the implants 100, 300, 400, 600, 700, 800, 900, 1000, 1100, and 1200 formed according to the present disclosure can adequately support the surrounding anatomical structures without an abnormal risk of fracturing surrounding bone following implantation.

In some exemplary embodiments, a method of forming an orthopaedic implant with a patient-adjusted stiffness is provided. As used herein, a "patient-adjusted" stiffness may refer to a stiffness of an implant that is provided for a specific patient, i.e., a single patient, or a specific patient population, i.e., a population of patients that share common medically significant characteristics, such as having osteoporosis, scoliosis, and/or arthritis. To form the implant, such as the orthopaedic implant 100, an amount of stiffness that the implant requires to treat a patient is determined. Determining the stiffness may include, for example, evaluating a condition of the patient anatomy and a medical history of the patient. The determining may include visualizing the patient anatomy at an implantation site using, for example, magnetic resonance imaging (MRI) or x-ray imaging techniques to determine the progression of disease in the patient as well as the shape of anatomical features surrounding the implantation site. In some embodiments, determining the stiffness may include comparing the condition of the patient anatomy to comparable patient anatomies and deriving the stiffness from the comparison. It should thus be appreciated that many different techniques may be used to determine the stiffness required to treat the patient. In some embodiments, the required stiffness may be similar to the stiffness of the native anatomical structures of the patient, e.g., vertebrae of the patient, so the produced implant has a "modulus match" with the anatomy of the patient.

Once the required stiffness is determined, the implant may be formed such that the formed implant has the required stiffness. In some embodiments, forming the implant includes providing an implant having a shape and modifying the implant to have the required stiffness. Modifying the implant may include, for example, forming one or more stiffness adjusting features in the implant, as previously described. Modifying the implant may also include adjusting a material forming one or more regions of the implant, such as porous ingrowth material regions or an intermediate region, by, for example, changing the porosity, changing the shape, or changing the composition of the adjusted material. After the implant is formed with the required stiffness, the implant may be delivered to a healthcare provider, such as a surgeon, and implanted within a patient at an implantation site.

From the foregoing, it should be appreciated that the present disclosure provides methods for producing implants with an appropriate stiffness for the desired application. The method allows production of implants that are not so stiff that abnormal bone fracturing becomes a significant issue while also providing sufficient support for the surrounding anatomical structures. Thus, implants can be produced with an appropriate stiffness to heal the patient without significantly increasing the risk of detrimental effects, such as abnormal bone fracturing, following implantation.

Figure 13:
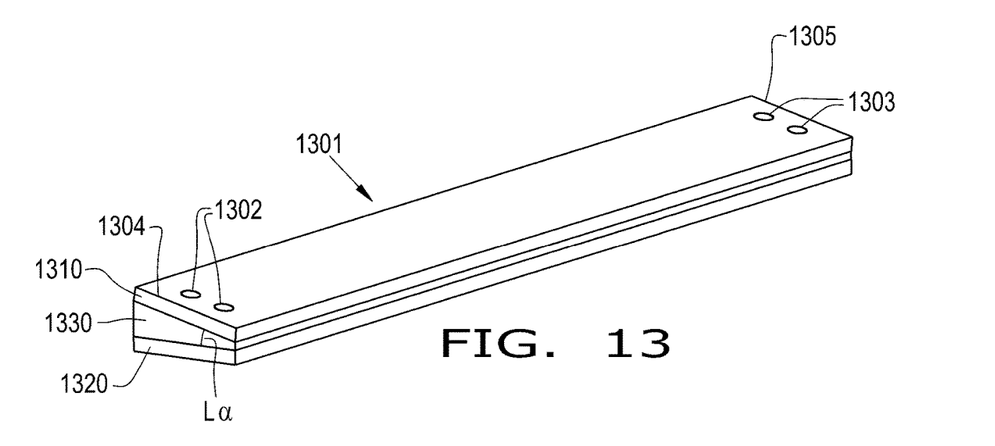
FIG. 13 is a perspective view of an exemplary embodiment of a strip of material that may be used to form a plurality of orthopaedic implants, provided according to the present disclosure.
Figure 14:
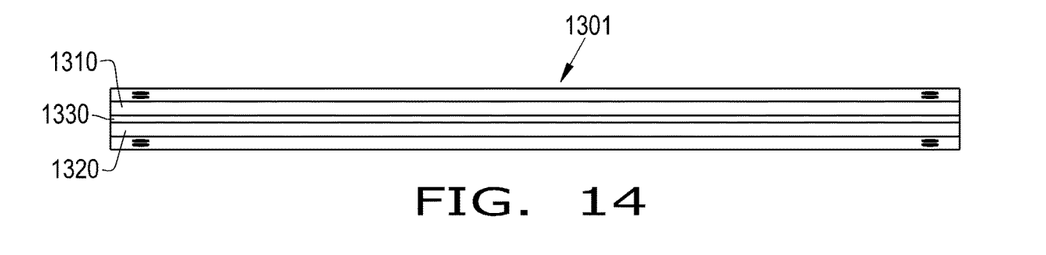
FIG. 14 is a front view of the strip of material of FIG. 13.
Figure 15:
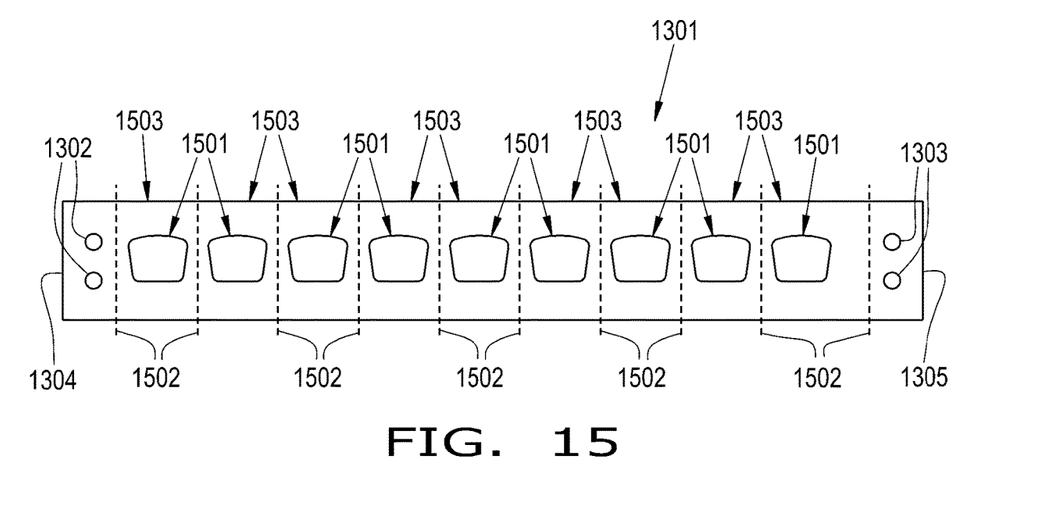
FIG. 15 is a top view of the strip of material of FIGS. 13-14 with a plurality of through-openings formed therein and illustrated cleave lines.

In some embodiments, a method of manufacturing multiple orthopaedic implants, such as the implant 300 illustrated in FIG. 3, is provided. Each of the produced implants may have similar stiffness and shapes, as will be appreciated from the further description provided herein. Referring specifically now to FIGS. 13-15, it can be seen that the method may include producing a strip 1301 of material that will be used to form the implant 300. The strip 1301 of material may be, for example, a composite of a first porous ingrowth material 1310, a second porous ingrowth material 1320, and a porous intermediate material 1330 disposed between the ingrowth materials 1310, 1320. The intermediate material 1330 may be formed with a top surface and a bottom surface that defines the lordotic angle La of the implant 300, as previously described. In some embodiments, a plurality of holding openings 1302, 1303 are formed on opposite ends 1304, 1305 of the strip 1301 for holding the strip 1301 with, for example, clamps.

Referring specifically now to FIG. 15, it can be seen that a plurality of through-openings 1501 have been formed in the strip 1301. Each of the through-openings 1501 corresponds to an implant that will be formed from the strip 1301, i.e., nine through-openings 1501 are formed in the strip 1301, corresponding to nine implants being formed from the strip 1301. The through-openings 1501 may be formed in the strip 1301 in any suitable fashion such as, for example, punching, machining, etc. In some embodiments, the materials 1310, 1320, 1330 forming the strip 1301 have openings formed therein prior to bonding to produce the through-openings 1501 through the strip 1301.

To form implants from the strip 1301, individual implants are cut from the strip 1301 into the shape of the final implant. As illustrated in FIG. 15, for example, the strip 1301 can be cut along cleave lines 1502 to form a plurality of implant blanks 1503. After the implant blanks 1503 are separated from one another, the implant blanks 1503 may be machined, if necessary, to the final implant shape or packaged and sterilized before being shipped for implantation. In some embodiments, one or more of the implant blanks 1503 can also be processed to adjust a stiffness the final implant, as previously described.

Figure 16:
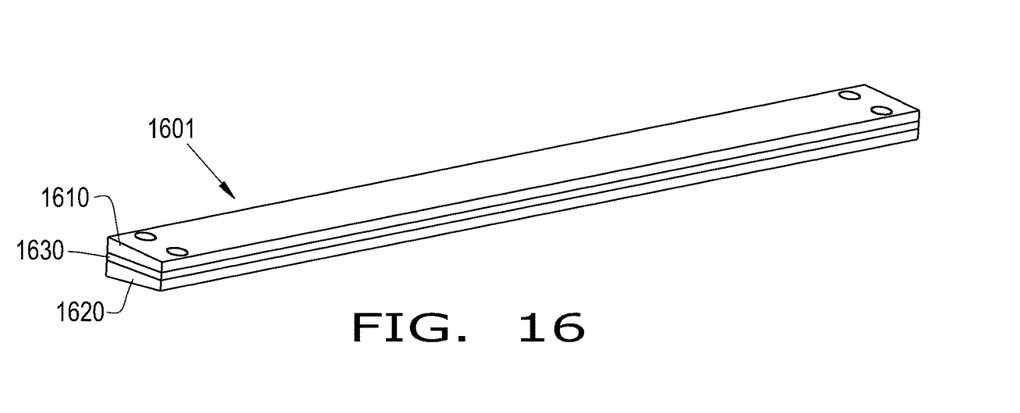
FIG. 16 is a perspective view of another exemplary embodiment of a strip of material may be used to form a plurality of orthopaedic implants, provided according to the present disclosure.

Referring now to FIG. 16, another exemplary embodiment of a strip 1601 that may be used to make flat implants, i.e., implants without a lordotic angle, is illustrated for producing, for example, the implant 100 illustrated in FIGS. 1-2. The strip 1601 is formed to have a first porous ingrowth material 1610, a second porous ingrowth material 1620, and a porous intermediate material 1630 disposed between the ingrowth materials 1610, 1620. The porous intermediate material 1630 is provided with a flat top surface and a flat bottom surface so the produced implants do not define a lordotic angle. In all other respects, the strip 1601 may be used to produce several individual implants similarly to the previously described strip 1301.

From the foregoing, it should be appreciated that the present disclosure provides methods for manufacturing multiple implants from a single material source, which may be a strip, a sheet, or a blank. The material source may be kept readily on hand by a manufacturer and, when needed, processed to produce implants with the desired shape and stiffness. Strips of material, for example, may be kept on hand by a manufacturer to produce implants, as needed, reducing the need for storing many different materials. It should thus be appreciated that the previously described method may increase manufacturing speed and reduce manufacturing cost by providing an easily handled and processed material that can be rapidly processed to produce one or more implants.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A method of manufacturing multiple orthopaedic implants, the method comprising:
   producing a strip of material comprising a composite of a first porous ingrowth material and a second porous ingrowth material, wherein the strip of material further comprises a porous intermediate material disposed between the first porous ingrowth material and the second porous ingrowth material;
   forming a plurality of through-openings in the strip; and
   cutting a plurality of implant blanks from the strip, each of the implant blanks comprising at least one of the formed through-openings.

2. The method of claim 1, wherein the intermediate material is formed with a top surface and a bottom surface that define a lordotic angle of each of the implant blanks.

3. The method of claim 1, wherein the intermediate material comprises a flat top surface and a flat bottom surface.

4. The method of claim 1, wherein each of the implant blanks has a similar shape.

5. The method of claim 1, wherein the strip has a plurality of holding openings formed on opposite ends of the strip.

6. The method of claim 1, wherein each of the implant blanks comprises one of the formed through-openings such that a number of the through-openings formed in the strip is equal to a number of the implant blanks cut from the strip.

7. The method of claim 1, further comprising processing at least one of the implant blanks to adjust a stiffness of a final implant formed from the at least one processed implant blank, wherein the processing comprises removing material from the at least one of the implant blanks.

8. The method of claim 1, further comprising machining at least one of the implant blanks to a final implant shape.

9. The method of claim 1, further comprising machining at least one of the implant blanks to a final implant shape.

10. A method of manufacturing multiple orthopaedic implants, the method comprising:
producing a strip of material comprising a composite of a first porous ingrowth material and a second porous ingrowth material, wherein the strip has a plurality of holding openings formed on opposite ends of the strip;
forming a plurality of through-openings in the strip; and
cutting a plurality of implant blanks from the strip, each of the implant blanks comprising at least one of the formed through-openings.

11. The method of claim 10, wherein the strip of material further comprises an intermediate material disposed between the first porous ingrowth material and the second porous ingrowth material.

12. The method of claim 11, wherein the intermediate material is formed with a top surface and a bottom surface that define a lordotic angle of each of the implant blanks.

13. The method of claim 11, wherein the intermediate material comprises a flat top surface and a flat bottom surface.

14. The method of claim 10, wherein each of the implant blanks has a similar shape.

15. The method of claim 10, wherein each of the implant blanks comprises one of the formed through-openings such that a number of the through-openings formed in the strip is equal to a number of the implant blanks cut from the strip.

16. The method of claim 10, further comprising processing at least one of the implant blanks to adjust a stiffness of a final implant formed from the at least one processed implant blank, wherein the processing comprises removing material from the at least one of the implant blanks.

* * * * *

UNITED STATES PATENT AND TRADEMARK OFFICE
CERTIFICATE OF CORRECTION

PATENT NO. : 11,918,478 B2
APPLICATION NO. : 17/391243
DATED : March 5, 2024
INVENTOR(S) : Stalcup et al.

Page 1 of 1

It is certified that error appears in the above-identified patent and that said Letters Patent is hereby corrected as shown below:

In the Specification

Column 4
At Line 33, please delete "angle La.", and substitute therefore --angle Lα.--;
At Line 41, please delete "angle La", and substitute therefore --angle Lα--;
At Line 44, please delete "angle La", and substitute therefore --angle Lα--; and
At Line 47, please delete "angle La", and substitute therefore --angle Lα--.

Column 9
At Line 35, please delete "angle La", and substitute therefore --angle Lα--.

Signed and Sealed this
Twenty-seventh Day of January, 2026

John A. Squires
*Director of the United States Patent and Trademark Office*